(12) United States Patent
Kozawa et al.

(10) Patent No.: US 9,595,426 B2
(45) Date of Patent: Mar. 14, 2017

(54) METHOD AND SYSTEM FOR MASS SPECTROMETRY DATA ANALYSIS

(75) Inventors: Hiroaki Kozawa, Shiga (JP); Shinichi Yamaguchi, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 554 days.

(21) Appl. No.: 14/349,425

(22) PCT Filed: Oct. 7, 2011

(86) PCT No.: PCT/JP2011/073196
§ 371 (c)(1),
(2), (4) Date: Apr. 3, 2014

(87) PCT Pub. No.: WO2013/051148
PCT Pub. Date: Apr. 11, 2013

(65) Prior Publication Data
US 2014/0249766 A1    Sep. 4, 2014

(51) Int. Cl.
G01N 31/00 (2006.01)
H01J 49/00 (2006.01)
G06F 19/00 (2011.01)

(52) U.S. Cl.
CPC ........ H01J 49/0036 (2013.01); G06F 19/703 (2013.01)

(58) Field of Classification Search
CPC .......... G01N 2570/00; G01N 2800/52; G01N 33/57438; G01N 13/00; G01N 15/08; G01N 1/02; G01N 1/04; G01N 1/405; G01N 2001/028; G01N 2013/006;
(Continued)

(56) References Cited

U.S. PATENT DOCUMENTS 7,473,892 B2 *  1/2009  Sano ............... G01N 33/6848
                                                           250/281
2010/0029552 A1 *  2/2010  Watt .................. C07K 14/00
                                                           514/12.2

FOREIGN PATENT DOCUMENTS

JP    2006-17570 A    1/2006
JP    2007-287531 A   11/2007

OTHER PUBLICATIONS

International Search Report for PCT/JP2011/073196 dated Dec. 27, 2011.

(Continued)

*Primary Examiner* — Roy Y Yi
(74) *Attorney, Agent, or Firm* — Sughrue Mion, PLLC (57) ABSTRACT

In estimating a structural formula of an unknown substance produced through partial structural change of an original substance having a known structure caused by metabolism or the like, structural change is considered in two stages, the elimination of a partial structure and the addition of another partial structure. First, an additional partial structure is collected as known information in addition to an $MS^n$ spectrum of the unknown substance and a structural formula of the original substance. A structural formula at the time when a partial structure is eliminated from the original substance is estimated, and a structural formula of each of product ions is estimated. The structural formula of the unknown substance is determined by estimating a structure that can produce the candidates for structural formulas of the product ions by dissociation.

9 Claims, 4 Drawing Sheets (58) Field of Classification Search
CPC ..... G01N 2015/0065; G01N 2015/086; G01N 21/658; G01N 2333/47
See application file for complete search history.

(56) References Cited

OTHER PUBLICATIONS

European Extended Search Report issued Apr. 15, 2015 in European Patent Application No. 11873617.2.

* cited by examiner

METHOD AND SYSTEM FOR MASS SPECTROMETRY DATA ANALYSIS

CROSS REFERENCE TO RELATED APPLICATIONS

This application is a National Stage of International Application No. PCT/JP2011/073196 filed Oct. 7, 2011, the contents of which are incorporated herein by reference in their entirety.

TECHNICAL FIELD

The present invention relates to a method and a system for data analysis for analyzing the chemical structure of a substance by performing analysis of $MS^n$ spectrum data obtained with an $MS^n$ mass spectrometer (where n is equal to or greater than 2) or $MS^1$ spectrum data obtained by utilizing in-source decay (ISD) or the like and more particularly relates to a method and a system for mass spectrometry data analysis for estimating the structure of an unknown substance that is produced through partial structural change caused by some reason from a substance having a known structure or an unknown substance the structure of which is largely in common with and only partially differs from that of a substance having a known structure.

BACKGROUND ART

In recent years, mass spectrometers capable of performing $MS^n$ analysis are widely used for structure analysis of various polymer compounds including protein. Specifically, when an ion originating from a substance of interest contained in a sample is dissociated by collision induced dissociation (CID), a molecular bond is broken at a specific site depending on the bond energy or other factors, and various product ions and neutral losses are produced. Therefore, an ion having a specific mass-to-charge ratio m/z corresponding to a substance of interest is selected from various ions produced from a sample, the selected ion is dissociated by CID, and various product ions (fragment ions) produced by the dissociation are subjected to mass spectrometry to obtain an $MS^2$ spectrum. Since the $MS^2$ spectrum includes information about various fragments (including product ions and neutral losses) originating from the substance of interest, the chemical structure of the substance of interest can be estimated by analyzing the $MS^2$ spectrum data. In the case where the ion cannot be dissociated into sufficiently small mass-to-charge ratios by only one time of the CID operation, the structural analysis of the substance of interest utilizing the $MS^n$ spectrum (where n is equal to or greater than 3) obtained by repeating the CID operation a plurality of times is sometimes performed.

On the other hand, in a mass spectrometer equipped with an ion source by electron ionization (EI) or the like, a peak of a product ion or peaks of product ions fragmented from an ion originating from a sample component can be obtained in an $MS^1$ spectrum by a method called in-source decay. Therefore, there sometimes occurs a case that the structural analysis of the substance of interest can be performed utilizing the $MS^1$ spectrum in which a product ion or ions originating from the substance of interest is observed as described here instead of utilizing the $MS^n$ spectrum. Hereinafter, the $MS^1$ spectrum and the $MS^n$ spectrum (where n is equal to or greater than 2) in both of which a product ion or ions are observed are together simply referred to as the $MS^n$ spectrum.

The most general method for estimating the structure of an unknown substance using the $MS^n$ spectrum is a database search utilizing the comparison of the $MS^n$ spectrum pattern. Specifically, the compound name, the molecular weight, the composition formula, structural formula, the $MS^n$ spectrum pattern, and other data are registered in a database (sometimes referred to as a library) for identification with regard to various known compounds, and when a measured $MS^n$ spectrum is obtained for an unknown substance, the unknown substance is identified and the structural formula is drawn out by searching, on the database, for a compound the peak pattern of which matches or similar to the measured $MS^n$ spectrum under a predetermined search condition. For such an identification database, databases created by users themselves, and various existing databases that are open to the public provided by public institutions are utilized.

Though the amount of data stored in the identification database as described above is generally huge, all the compounds that may become the object of analysis are not stored in the database. For example, among agricultural chemicals, pharmaceuticals, or metabolites produced in vivo from such substances, there exist many analogous compounds in which the basic skeletons of the compounds are common but only a part of the structure is substituted (for example, a methyl group is substituted with an ethyl group, or chloride is substituted with bromide). It is practically impossible to store all such compounds in the identification database. Therefore, it often occurs that a substance cannot be identified and the structural formula cannot be determined even if the database search is performed for such a compound.

In order to solve the problem, in the method for mass spectrometry data analysis method described in Patent Literature 1, in analyzing the structure of the unknown substance the structure of which is known to be similar to the structure of a known substance having a known structure, the structure of an unknown substance is estimated by a combination of a fragment prediction and a known structural change pattern, where the fragment prediction is a prediction of fragments for a peak or peaks having a mass-to-charge ratio or ratios m/z appearing commonly in $MS^n$ spectra of a known substance and in an unknown substance. The "structural change pattern" is the information about replacement of substituents, addition of a component, elimination of a component, or the like. Owing to such estimation, it becomes possible to identify and determine the structural formula for a compound that is not stored in the identification database.

However, in the method for mass spectrometry data analysis described in Patent Literature 1, the structure cannot be estimated for an unknown substance in which a structural change that is not registered as a structural change pattern has occurred. For example, the structure of a drug metabolite is considered to have a structure formed in such a way that a partial structure in a substance before metabolism eliminates and then another partial structure is added to the elimination site or another site different from the elimination site. In this case, the eliminating partial structure varies widely depending on the substance before the metabolism, and it is difficult to register all the eliminating partial structures as structural change patterns in advance. For such a substance, therefore, it is likely to occur that the structure of an unknown substance cannot be determined.

CITATION LIST

Patent Literature

[Patent Literature 1] JP-A 2007-287531

SUMMARY OF INVENTION

Technical Problem

The present invention has been developed to solve the aforementioned problem, and the object is to provide a method and a system for mass spectrometry data analysis capable of estimating the structure of an unknown substance that is similar to a substance having a known structure or is produced from the substance having a known structure by a part of the structural changed, based on an $MS^n$ spectrum data efficiently and with high reliability even when the pattern of a structural change, such as that associated with metabolism or the like, is not prepared in a database or the like in advance.

Solution to Problem

The first aspect of the present invention aimed at solving the aforementioned problem is a method for mass spectrometry data analysis for estimating the structure of an unknown substance produced through partial structural change from a known substance having a known structure based on $MS^n$ spectra (where n is an integer equal to or greater than 1) obtained by performing mass spectrometry of product ions produced by dissociating, in one or a plurality of times, a precursor ion or ions originating from the unknown substance, the method including:

a) an additional partial structure information obtaining step of obtaining pre-given information of an additional partial structure that can be added to the known substance in association with the structural change;

b) a post-elimination structure estimating step of estimating a post-elimination structural formula after an unknown eliminating partial structure is eliminated from the known substance in association with the structural change, the estimation being performed based on pre-given information about the structural formula of the known substance, information about an additional partial structure obtained in the additional partial structure information obtaining step, and information about the mass of the precursor ion from the unknown substance obtained from a mass spectrum of the unknown substance;

c) a product ion structure estimating step of estimating a structural formula of each of product ions by searching for coincidence of combined masses of a trunk partial structure and the additional partial structure and masses of product ions obtained from an $MS^n$ spectrum or $MS^n$ spectra of the unknown substance, the trunk partial structure being derived from a structure shown by a structural formula of candidates for the post-elimination structure formula estimated in the post-elimination structure estimating step, and listing candidates for structural formulas of the product ions; and d) an unknown substance structure determining step of determining a structural formula of the unknown substance by searching, based on the candidates for structural formulas of the product ions estimated in the product ion structure estimating step, for a structural formula that can produce the candidates for the structural formulas of product ions by dissociation.

The second aspect of the present invention aimed at solving the aforementioned problem is a system for carrying out a method for mass spectrometry data analysis according to the first aspect of the present invention and is a system for mass spectrometry data analysis for estimating the structure of an unknown substance produced through partial structural change from a known substance having a known structure based on $MS^n$ spectra (where n is an integer equal to or greater than 1) obtained by performing mass spectrometry of product ions produced by dissociating, in one or a plurality of times, a precursor ion or ions originating from the unknown substance, the system including:

a) an additional partial structure information obtaining unit of obtaining pre-given information of an additional partial structure that can be added to the known substance in association with the structural change;

b) a post-elimination structure estimating unit of estimating a post-elimination structural formula after an unknown eliminating partial structure is eliminated from the known substance in association with the structural change, the estimation being performed based on pre-given information about the structural formula of the known substance, information about an additional partial structure obtained by the additional partial structure information obtaining unit, and information about the mass of the precursor ion from the unknown substance obtained from a mass spectrum of the unknown substance;

c) a product ion structure estimating unit of estimating a structural formula of each of product ions by searching for coincidence of combined masses of a trunk partial structure and the additional partial structure and masses of product ions obtained from an $MS^n$ spectrum or $MS^n$ spectra of the unknown substance, the trunk partial structure being derived from a structure shown by a structural formula of candidates for the post-elimination structure formula estimated in the post-elimination structure estimating unit, and listing candidates for structural formulas of the product ions; and d) an unknown substance structure determining unit of determining a structural formula of the unknown substance by searching, based on the candidates for structural formulas of the product ions estimated by the product ion structure estimating unit, for a structural formula that can produce the candidates for the structural formulas of product ions by dissociation.

In the first and second aspects of the present invention, the "unknown substance" to be analyzed for the structure is, for example, a substance produced from a substance having a known structure through chemical change such as metabolism. Alternatively, the unknown substance may be a byproduct produced in synthesis or the like of a known substance, through partial replacement or loss, or addition of another component in the structure of the known substance.

Moreover, the $MS^n$ spectrum where n is equal to 1, i.e. an $MS^1$ spectrum ($MS^1$ mass spectrum) is a result of performing a mass spectrometry of a product ion produced by performing fragmentation (dissociation) of an ion originating from the substance of interest by in-source decay, and the $MS^n$ spectrum where n is equal to or greater than 2 is the result of performing mass spectrometry of a product ion produced by performing one or a plurality of times of dissociating operations by CID or the like.

Specifically, as described above, while a substitution pattern or the like of a partial structure that changes in association with metabolism or the like has been used as a structural change pattern in the conventional technique described in Patent Literature 1, the substitution of the partial structure is considered separately in two stages, the elimination and the addition of a partial structure in the first and second aspects of the present invention. When the structural change of a substance by drug metabolism or the like is considered, the eliminating partial structure depends on the structure of the original substance (i.e. substance before elimination), the reaction condition, or other factors, therefore generally varies considerably widely, and the prediction of the eliminating partial structure is difficult. On the other hand, the partial structure to be added mostly depends on the kind of metabolism and is quite narrowed, and therefore the prediction of the partial structure to be added is easy. Therefore, for example, a user estimates the partial structure to be added in advance and inputs it (or selects one from options of a plurality of partial structures prepared in advance), thereby information about the additional partial structure is given.

The post-elimination structure estimating unit in the system for mass spectrometry data analysis according to the second aspect of the present invention calculates the mass of the post-elimination structural formula after the unknown eliminating partial structure is eliminated from the known substance from the mass of the additional partial structure determined from the information about the additional partial structure (e.g., composition formula) and the mass of the unknown substance determined from the information about the mass of the precursor ion originating from the unknown substance, and estimates the post-elimination structural formula from the mass and the information about the structural formula of the known substance. In the case where the post-elimination structural formula is not narrowed to one, a plurality of candidates for the post-elimination structural formula may be listed. However, since the post-elimination structural formula cannot always be obtained, a method of utilizing another $MS^n$ spectrum obtained by changing the analysis conditions, for example, as described later is considered in the case where a post-elimination structural formula cannot be obtained at all.

The product ion structure estimating unit estimates the structural formula of each of product ions originating from the unknown substance by comparing the combined mass of the trunk partial structure that can be estimated from the candidate for the post-elimination structural formula with the additional partial structure, and the mass of the product ion corresponding to each peak on the $MS^n$ spectrum of the unknown substance. Here, in the case where the structural formula for one product ion cannot be narrowed to one, a plurality of candidates for the structural formula of the product ion may be listed. Since each product ion determined from the $MS^n$ spectrum of the unknown substance is produced by the dissociation of the unknown substance, the unknown substance structure estimating unit can estimate the structural formula of the unknown substance by estimating the aspect of the dissociation that can produce the structure from a plurality of candidates for the structural formula of product ion.

Of course, in the case where other information about the known substance or the unknown substance is known, the reliability of the estimation can be improved or the processing speed can be enhanced by adding the process utilizing the information additionally in the first and second aspects of the present invention.

For example when the $MS^n$ spectrum of the known substance is given as the additional information, the narrowing in estimating the structural formula of the unknown substance can be performed by estimating which site of the known substance the additional partial structure has been added to by comparing, for example, the product ion originating from the known substance determined from the $MS^n$ spectrum, with the product ion originating from the unknown substance determined from the $MS^n$ spectrum of the unknown substance.

Moreover, when the composition formula of the unknown substance is given as the additional information, the composition of the additional partial structure is originally known, and therefore the composition of the eliminating partial structure becomes clear from the difference between the composition formula of the unknown substance and the composition of the additional partial structure. Thereby, it becomes possible to narrow the candidates for the post-elimination structural formula. Furthermore, when the composition formula or the structural formula of at least one product ion originating from the unknown substance is given as the additional information, the structural formula estimation for some product ion becomes unnecessary or it becomes possible to narrow the structural formula. Moreover, the result is considered to be narrowed by the selection of the intermediate data (the combination of the eliminating partial structure that is estimated or the partial structure after elimination corresponding to the product ion with the additional partial structure) by a user.

Moreover, as one mode of the method for mass spectrometry data analysis method according to the first aspect of the present invention, in the case where there exist a plurality of candidates for the post-elimination structural formulas estimated in the post-elimination structure estimating step, the structural formula of the unknown substance may be estimated for each of the plurality of candidates for the post-elimination structural formulas in the product ion structure estimating step and the unknown substance structure estimating step and the plurality of candidates for the structural formula may be determined. Thereby, omissions in estimating the candidate for the structural formula of the unknown substance can be reduced. Moreover, in the case where there exist a plurality of candidates for the structural formula of the unknown substance, the candidates for the structural formula may be ranked in descending order of probability and the candidates for the structural formula is output together with the ranking. In ranking the candidates for the structural formula of the unknown substance, information calculated theoretically such as a level of the intramolecular bond energy in addition to information obtained in the analysis such as the extent of coincidence of the mass in determining the candidates for the structural formula of product ion may be utilized.

Moreover, as another mode of the method for mass spectrometry data analysis according to the first aspect of the present invention, the structural formula of the unknown substance may be estimated after determining, as a candidate for the structural formula of one product ion from the unknown substance, the estimated structural formula obtained by performing each of the steps for the $MS^{n+1}$ spectrum obtained from the $MS^{n+1}$ analysis performed using an ion having a specific mass-to-charge ratio in the $MS^n$ spectrum of the unknown substance as a precursor ion. Thereby, even in the case where the structure of the unknown substance cannot be specified based on the $MS^2$ spectrum data for example, it becomes possible to specify the structure of the unknown substance with high reliability based on the $MS^3$ or $MS^4$ spectrum data obtained by repeating the dissociating operation.

Moreover, in the method for mass spectrometry data analysis according to the first aspect of the present invention, each of the candidates for the structural formula of the unknown substance may be determined in each of the steps using a plurality of MS$^n$ spectra obtained under the different analysis conditions for the unknown substance, and the structure with high probability may be extracted by putting the results together and may be output as a estimation result of the structural formula of the unknown substance. The analysis condition here includes the dissociation condition. Since the mode of the dissociation changes when the analysis condition is changed, different MS$^n$ spectra are obtained from the same unknown sample. In the case where the candidates for the structural formula thus determined utilizing a plurality of MS$^n$ spectra different from one another are identical, it is highly possible that the candidate is the right structural formula. Accordingly, by the above-described method, even when the structure of the unknown substance is complicated, the structural formula of the unknown substance can be estimated with high reliability.

Advantageous Effects of Invention

According to the method and the system for mass spectrometry data analysis according to the present invention, even in the case where the unknown substance produced through partial change of the structure of a known substance caused by a chemical change such as, for example, metabolism is not stored in an identification database, a structural formula of the unknown substance can be estimated efficiently and with high reliability. Moreover, even when a structural change pattern associated with a structural change such as metabolism is unknown, a structural formula of an unknown substance can be estimated with high reliability as long as a partial structure to be added in association with the structural change is known or can be estimated with high accuracy.

DESCRIPTION OF EMBODIMENTS

Figure 1:
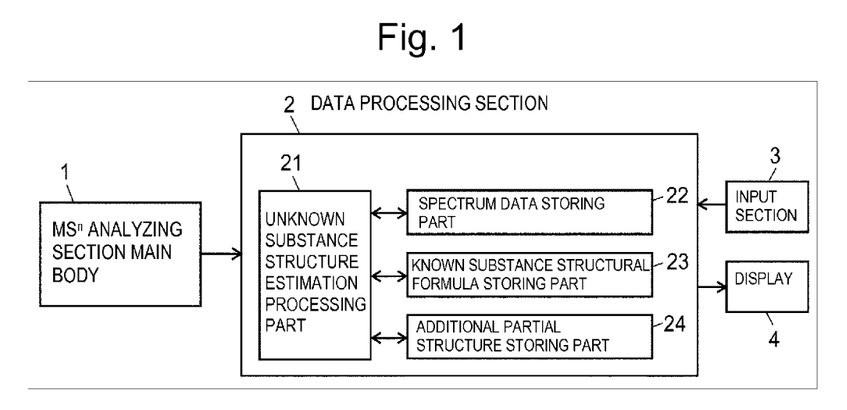
FIG. 1 is a schematic configuration diagram of a mass spectrometry system including an apparatus for mass spectrometry data analysis according to an embodiment of the present invention.

One embodiment of the mass spectrometry system including the apparatus for mass spectrometry data analysis according to the present invention will now be described with reference to the accompanying drawings. FIG. 1 is a schematic configuration diagram of the mass spectrometry system according to the present embodiment.

An MS$^n$ analyzing section main body 1 includes, although not shown in the figure, an ion source, an ion trap, a time-of-flight mass spectrometer (TOFMS), and an ion detector etc., performs MS$^n$ analysis using an ion, as a precursor ion, having a specific mass-to-charge ratio m/z among various ions produced from a sample and obtains an MS$^n$ spectrum data over a predetermined mass-to-charge ratio range. Typically, n is equal to 2, however, n may be equal to or greater than 3. In the case where the MS$^n$ analyzing section main body 1 has the constitution by which a product ion can be observed even in the ordinary MS$^1$ analysis by utilizing in-source decay, n may be 1. Typically, in-source decay of a molecular ion produced by ionization is likely to occur in the case where the ion source is EI. Except for EI, an ion source in a matrix-assisted laser desorption/ionization method, fast atom bombardment ionization, or the like can also produce relatively many product ions. In the case where only the MS$^2$ analysis is performed, a so-called triple quadrupole mass spectrometer can also be utilized instead of the combination of the ion trap and the TOFMS.

A data processing section 2 processing the MS$^n$ spectrum data obtained by an MS$^n$ analyzing section main body 1 comprises an unknown substance structure estimation processing part 21, a spectrum data storing part 22, a known substance structural formula storing part 23, and an additional partial structure storing part 24 as a functional block. The structural formulas of the various substances (compounds) are stored in the known substance structural formula storing part 23, and the above-described identification database can be utilized as the known substance structural formula storing part 23. On the other hand, the information about partial structures to be added to a substance in association with various structural changes such as in vivo metabolism, specifically additional partial structures, is stored in the additional partial structure storing part 24. Since most of the structures of the components to be added to a substance in various types of metabolism occurred, for example, in a human body are known, the kind of metabolism and the additional partial structure can be stored in such a way that both are associated with each other based on the known information.

Moreover, an input section 3 for operations by a user and a display 4 on which analysis results or the like are displayed are connected to a data processing section 2. The data processing section 2 can be made using a personal computer as a hardware resource so as to have the constitution by which each of the above-described functional blocks are embodied by performing a dedicated processing/control program installed in the personal computer.

The mass spectrometry system of the present embodiment is characterized by data analysis for estimating the structure of unknown substance having an unknown structure, such as a metabolite, a byproduct or a decomposition product, produced from a substance having a known structural formula (hereinafter, referred to as an "original substance") through partial structural change caused by some reason such as metabolism. Herein, although a metabolite produced from an original substance through metabolism will be described as an example, the structural change is not limited to the metabolism, and the mass spectrometry system is applicable for various types of structural change in which a part of the structure of an original substance changes.

Figure 2:
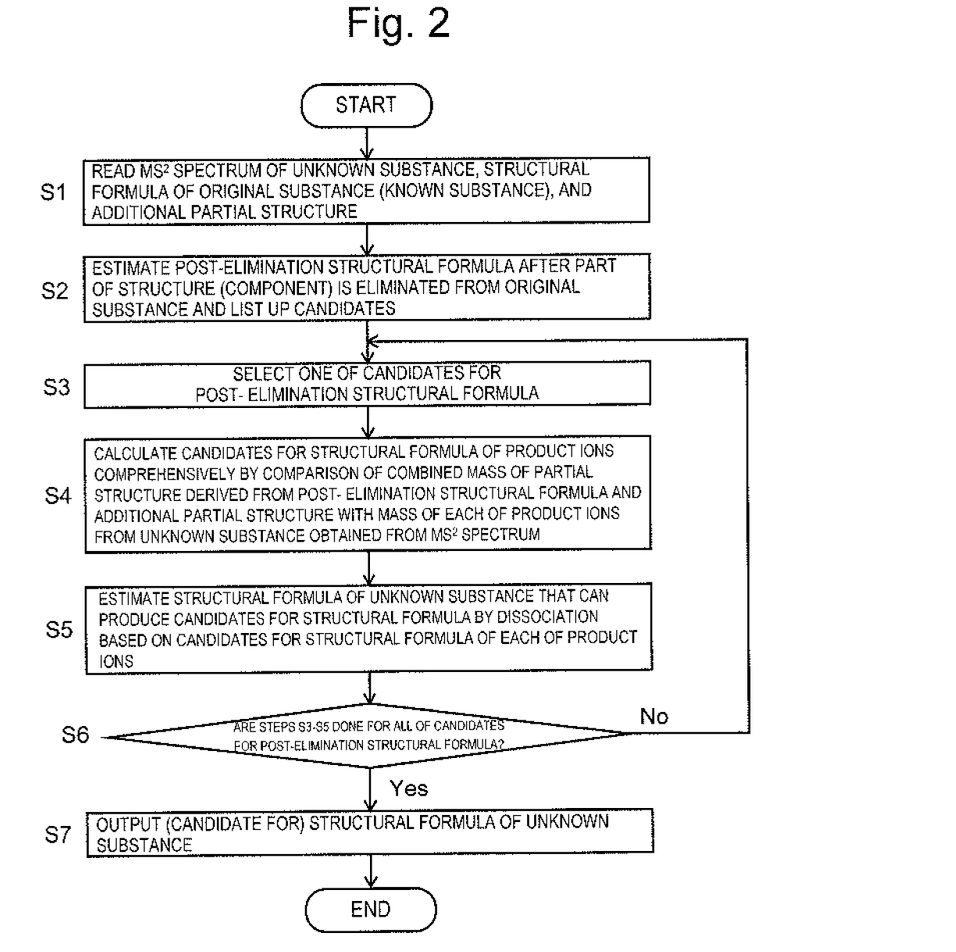
FIG. 2 is a flowchart of an exemplified procedure of an unknown substance structure estimating process performed in the mass spectrometry system of the embodiment.
Figure 3:
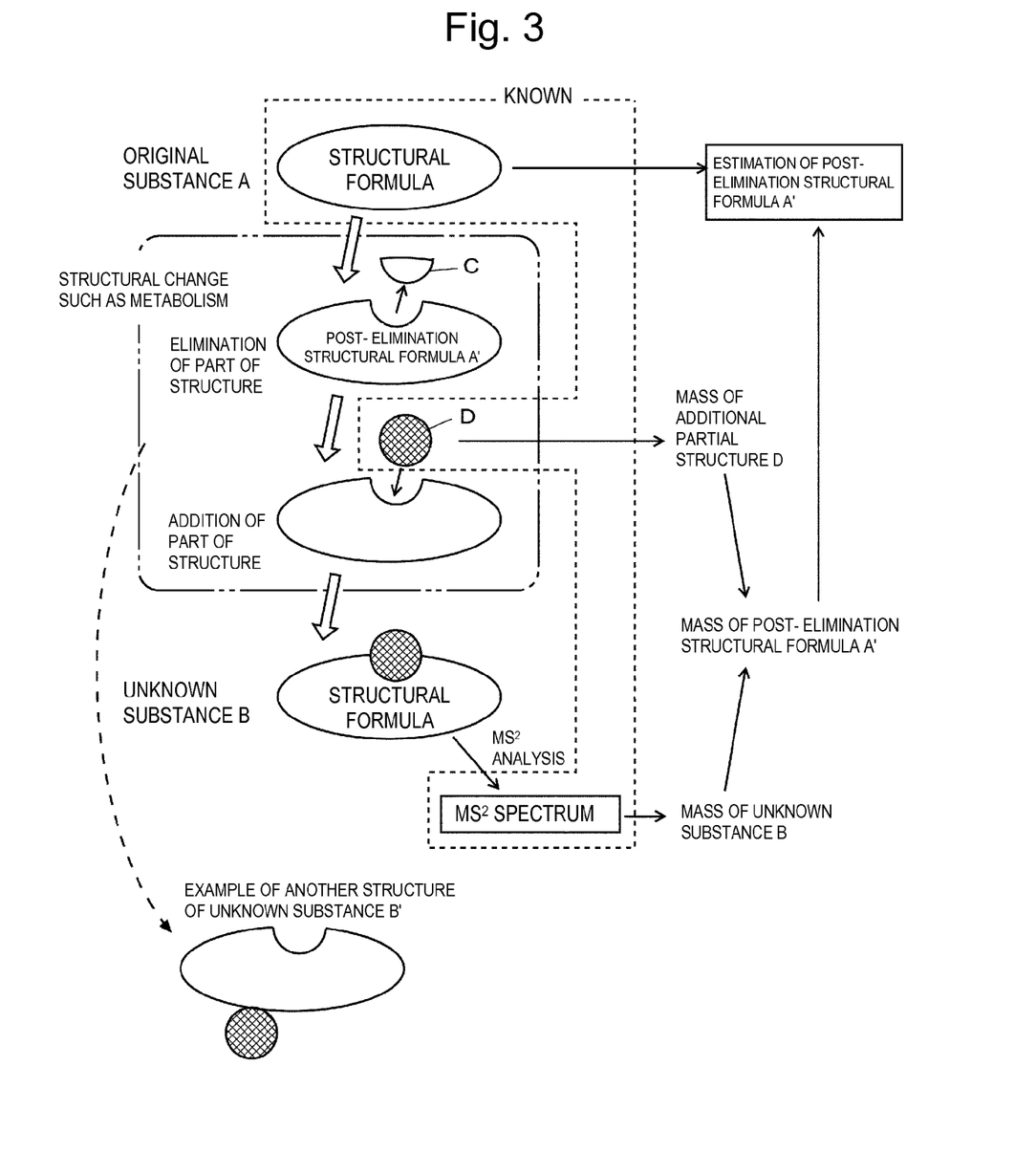
FIG. 3 is a conceptual diagram describing a model of structural change of a known substance and a method for estimating a post-elimination structural formula after a partial structure is eliminated in the mass spectrometry system of the embodiment.
Figure 4:
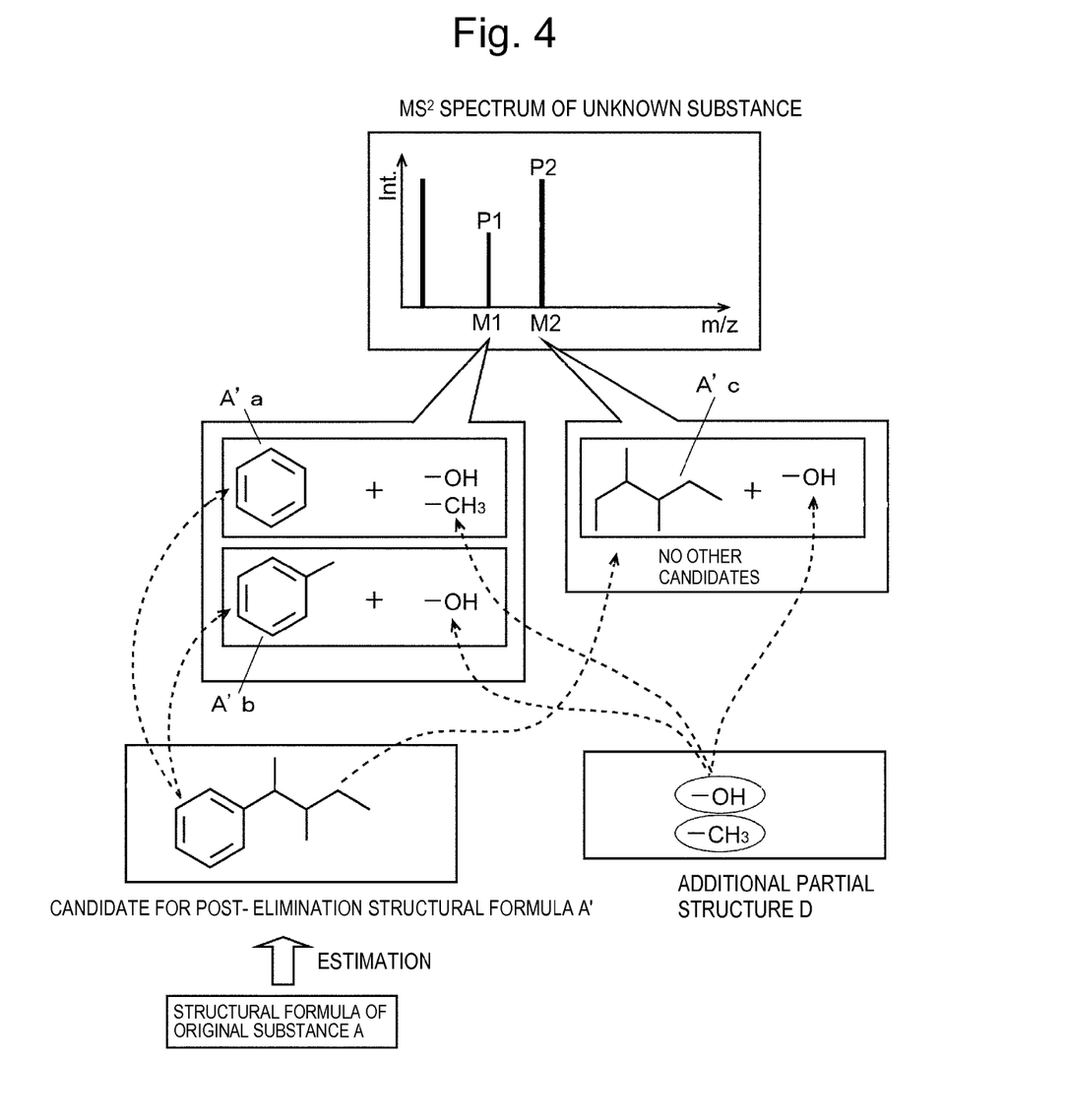
FIG. 4 is a conceptual diagram of unknown substance structure estimating process in the mass spectrometry system of the embodiment.

FIG. 2 is a flowchart of an exemplified procedure of a metabolite structure estimating process performed in the data processing section 2, FIG. 3 is a conceptual diagram describing a model of structural change of a known substance and a method for estimating a post-elimination structure after a partial structure is eliminated, and FIG. 4 is a conceptual diagram of the metabolite structure estimating process. The detail of the metabolite structure estimating process in the mass spectrometry system of the present embodiment is described by FIG. 2 to FIG. 4.

It is assumed that the MS$^2$ spectrum data which is a result of performing the MS$^2$ analysis using as a precursor ion an ion originating from the unknown substance contained in a sample that is an object of analysis is saved in the spectrum data storing part 22 at the process starting time.

When the process is started based on a user's instruction or the like from the input section 3, the unknown substance structure estimation processing part 21 reads an $MS^2$ spectrum data of the unknown substance that is an object of analysis from the spectrum data storing part 22, a structural formula data of an original substance from the known substance structural formula storing part 23, and an additional partial structure data to be added at the time of structural change from the original substance to the unknown substance from the additional partial structure storing part 24, respectively (step S1).

Since structural formula data of various compounds are stored in the known substance structural formula storing part 23, it becomes possible to read out the structural formula data of the original substance by designating a compound that is the original substance from the input section 3 by a user. Various additional partial structure data are also stored in the additional partial structure storing part 24, and an additional partial structure data that can be added corresponding to the metabolism or the like can be read out by giving information such as the kind of metabolism from the input section 3 by a user. Of course, a user may directly input the structural formula of the original substance and the additional partial structure from the input section 3 without utilizing the data stored in the known substance structural formula storing part 23 and the additional partial structure storing part 24.

Here, when an unknown substance B is produced from an original substance A having a known structure through structural change such as metabolism, it is considered, as illustrated in FIG. 3, that a two-stage action occurred, the first stage in which a partial structure C of some sort is eliminated from the original substance and the second stage in which an additional partial structure D is added to a structure A' after the partial structure is eliminated. The additional partial structure D is not always added to the site from which the partial structure is eliminated (i.e. replaced with a structurally eliminating group or the like), it sometimes occurs that the additional partial structure D is added to another site quite different from the elimination site as in the case of an unknown substance B'.

The structural formula of the original substance A, the additional partial structure D, and the $MS^2$ spectrum of the unknown substance B that are surrounded with a broken line in FIG. 3 are known information, specifically information that has already been given. The unknown substance structure estimation processing part 21 in the data processing section 2 first, based on the known information as described above, calculates a candidate for the structural formula (post-elimination structural formula) A' after the eliminating partial structure C is eliminated from the original substance A (step S2).

Specifically, the mass of the unknown substance B is determined from the mass-to-charge ratio m/z of the precursor ion in obtaining the $MS^2$ spectrum of the unknown substance B, and the mass of the additional partial structure D included in the unknown substance B is also determined from the structure that is known, and therefore the mass of the post-elimination structural formula A' is calculated from the difference. And the post-elimination structural formula A' can be estimated from the mass of the post-elimination structural formula A' and the structural formula of the original substance A that is known. Of course, since the unique structural formula cannot be determined conclusively in general, a plurality of candidates for the post-elimination structural formula A' that can be estimated are listed up.

In the case where the composition formula of the unknown substance B is given as the additional information besides the known information as described above, since the composition of the additional partial structure D is known, the composition corresponding to the post-elimination structural formula A' obtained by removing the additional partial structure D from the unknown substance B becomes clear. Accordingly, it is possible to narrow the candidates for the post-elimination structural formula A' using information about this composition, and the process after the narrowing can be simplified. Moreover, the selection of the post-elimination structural formula by a user may be performed.

Next, after selecting one candidate from among the candidates for the post-elimination structural formula A' calculated in the step S2 (step S3), the process of steps 4 to 5 is carried out for the selected candidate for the post-elimination structural formula A'.

First, since the post-elimination structural formula A' is considered to include a basic skeleton of the original material, the candidates for the structural formula of each of product ions produced by the dissociation of the unknown substance B are comprehensively calculated by combining the partial structure derived from one candidate for the post-elimination structural formula A' with the known additional partial structure (step S4). Specifically, since the site at which a bond is broken by CID in the post-elimination structural formula A' is unknown, various patterns are considered as a partial structure that can be produced from one candidate for the post-elimination structural formula A' by CID. In FIG. 4, three partial structures illustrated as A' a, A' b, and A' c among the candidates for the post-elimination structural formula A' are estimated. Also the number of the additional partial structures D is also not always one but sometimes more than one. Therefore, the masses obtained by combining the partial structure determined from the post-elimination structural formula A' with one of the additional partial structures D are comprehensively calculated, and the coincidence of each of the masses with the mass of each product ion that becomes clear from the mass-to-charge ratio of the peak appeared in the $MS^2$ spectrum of the unknown substance is evaluated.

The description is made using the example of FIG. 4. The mass-to-charge ratios of the peaks P1 and P2 appeared in the $MS^2$ spectrum of the unknown substance B are M1 and M2, respectively, and the mass of the product ion becomes clear from M1 and M2. The masses obtained by combining the partial structure of the post-elimination structural formula A' with the additional partial structure D (in this example, two kinds of the additional partial structure D, —OH and —$CH_3$) are calculated, and the coincidence with the mass of the product ion is evaluated. As a result, it is assumed that the masses of the two kinds of combination, [A'a]+[—$CH_3$, —OH] and [A'b]+[—OH], coincide with regard to the product ion of the peak P1, and one kind of the mass of [A'c]+[—OH] coincides with regard to the product ion of the peak P2. As described here, since only the coincidence of the mass is used as information for making a decision here, only one combination of the partial structure of the post-elimination structural formula A' with the additional partial structure D is not necessarily extracted for one product ion, it sometimes occurs that a plurality of combinations are extracted. In the case where the plurality of combinations are extracted, the plurality of combinations extracted may be listed as a candidate for the structural formula of the product ion.

In the case where the $MS^2$ spectrum of the original substance is given as the additional information besides the known information as described above, it is possible to estimate which partial structure the additional partial structure is added to by comparing the mass of the product ion obtained from the $MS^2$ spectrum of the original substance with the mass of the product ion obtained from the $MS^2$ spectrum of the unknown substance. Thereby, it becomes possible to narrow the candidates for the structural formula of the product ion, and the process after the narrowing can be simplified.

In the case where the composition formula or the structural formula of at least a part of the product ions originating from the unknown substance is given as the additional information besides the known information as described above, thereby it becomes possible to narrow the candidates for the structural formula of the product ion, and the process after the narrowing can be simplified.

If the candidates for the structural formula of each of product ions originating from the unknown substance B in the step 4 are listed, the combination that can be produced by the dissociation of the unknown substance B is found out by combining the candidates for the structural formula of the product ions and is selected as the structural formula of the unknown substance B (step S5). In addition, when the appropriate combination cannot be found out, it is because, for example, the candidate for the post-elimination structural formula A' selected in the step S3 is not appropriate, and therefore it may be concluded that there is no proper output. In the case where the structural formula of the unknown substance B is not narrowed to one, a plurality of structural formulas may be listed as candidates.

Next, whether the process of the steps S4 and S5 has been performed or not is decided with regard to all the candidates for the post-elimination structural formula A' obtained in the step S2 (step S6), and when there is an unprocessed candidate for the post-elimination structural formula A', the above-described steps S4 and S5 are carried out by returning to the step S3 and selecting the unprocessed candidate for the post-elimination structural formula A'. In the case where the decision is Yes in the step 6, the procedure proceeds to the step S7, then the structural formulas (or the candidates for the structural formula) of the unknown substance listed so far are output as an analysis result in the display 4.

In the data processing section 2 in the present embodiment as described above, the information about the additional partial structure D that is known in the structural change in estimating the structure of the unknown substance produced through structural change such as metabolism is utilized. The structural change patterns used in the above-described conventional technique includes information about not only the additional partial structure but also the eliminating partial structure C, the site from which the eliminating partial structure is eliminated, the site to which the additional partial structure D is added, and the like, and therefore is very diverse, and it is difficult to predict all the structural change patterns that can happen. On the other hand, as described above, the patterns are readily predictable from the kind of metabolism or the like when the included information is only the additional partial structure D and the kind of the patterns can be considerably narrowed. Accordingly, if the information about the additional partial structure D that can be added in association with the structural change is given for sure and the structure of the unknown substance can be estimated based on the information with high reliability and efficiently.

Particularly in the case where there exist a plurality of the candidates for the structural formula of the unknown substance, it is preferable to provide information together that helps a user make a decision as to which candidate is appropriate. Therefore, the plurality of the candidates for the structural formula may be ranked in descending order of probability, and the candidates for the structural formula may be output together with the ranking. In ranking the candidates for the structural formula of the unknown substance, information calculated theoretically such as a level of the intramolecular bond energy in addition to information obtained in the analysis such as, for example, the extent of coincidence of the mass in determining the candidate for the structural formula of the product ion may be utilized.

In the above embodiment, the analysis is performed based on the $MS^2$ analysis result. It also possible to perform analysis based on spectrum data obtained by $MS^n$ analysis associated with the dissociating operation in two or more times, i.e., $MS^n$ analysis where n is equal to or greater than 3. In the case where a spectrum data of MS3 or more is used as described here, the structural formula of the unknown substance may be estimated after the structural formula estimated by performing the process of the steps S2 to S6 for the $MS^{n+1}$ spectrum obtained by the $MS^{n+1}$ analysis performed using as a precursor ion an ion having a specific mass-to-charge ratio in the $MS^n$ spectrum of the unknown substance is designated to the candidate for the structural formula of one product ion from the unknown substance.

When the analysis conditions such as collision energy and the pressure of a CID gas in an ion trap (or a collision cell) are changed in the dissociating operation by CID, the mode of the dissociation is changed and it sometimes occurs that $MS^2$ spectra each having different patterns for the same unknown substance are obtained. The product ion is different when the $MS^2$ spectrum is different, and therefore, the process contents from S4 to S5 illustrated in FIG. 2 become different. However, the structural formula of the unknown substance B determined finally is supposed to be the same, and therefore when the structural formulas of a result of analysis based on the different $MS^2$ spectra are the same, it can be said that the reliability of the structural formula is high. Therefore, for example, the structural formulas that are derived from different $MS^2$ spectra obtained under different analysis conditions on an unknown substance and are the same may be output as a true structural formula. Moreover, such information may be utilized for the above-described ranking.

It is noted that the present embodiment is described as an example of the present invention, and it is evident that any modification, change or addition appropriately made within the spirit of the present invention will fall within the scope of appended claims.

REFERENCE SIGNS LIST

1 . . . $MS^n$ Analyzing Section Main Body
2 . . . Data Processing Section
21 . . . Unknown Substance Structure Estimation Processing Part
22 . . . Spectrum Data Storing Part
23 . . . Known Substance Structural Formula Storing Part
24 . . . Additional Partial Structure Storing Part
3 . . . Input Section
4 . . . Display

The invention claimed is:

1. A method for mass spectrometry data analysis for estimating a structure of an unknown substance produced through partial structural change from a known substance having a known structure based on MS$^n$ spectra (where n is an integer equal to or greater than 1) obtained by performing mass spectrometry of product ions produced by dissociating, in one or a plurality of times, a precursor ion or ions originating from the unknown substance, the method comprising:

a) an additional partial structure information obtaining step of obtaining pre-given information of an additional partial structure that can be added to the known substance in association with the structural change;

b) a post-elimination structure estimating step of estimating a post-elimination structural formula after an unknown eliminating partial structure is eliminated from the known substance in association with the structural change, the estimation being performed based on pre-given information about structural formula of the known substance, information about an additional partial structure obtained in the additional partial structure information obtaining step, and information about a mass of the precursor ion from the unknown substance obtained from a mass spectrum of the unknown substance;

c) a product ion structure estimating step of estimating a structural formula of each of product ions by searching for coincidence of a combined mass of a trunk partial structure and the additional partial structure and masses of product ions obtained from an MS$^n$ spectrum or MS$^n$ spectra of the unknown substance, the trunk partial structure being derived from a structure shown by a structural formula of a candidate for the post-elimination structural formula estimated in the post-elimination structure estimating step, and listing candidates for structural formulas of the product ions; and d) an unknown substance structure determining step of determining a structural formula of the unknown substance by searching, based on the candidates for structural formulas of the product ions estimated in the product ion structure estimating step, for a structural formula that can produce the candidates for the structural formulas of product ions by dissociation.

2. The method for mass spectrometry data analysis according to claim 1,
   wherein, in the case where an MS$^n$ spectrum of the known substance is given as additional information, narrowing of the structural formulas of product ions is performed by estimating which site of the known substance the additional partial structure has been added to by comparing product ions originating from the known substance determined from an MS$^n$ spectrum of the known substance with product ions originating the unknown substance determined from an MS$^n$ spectrum of the unknown substance in the product ion structure estimating step.

3. The method for mass spectrometry data analysis according to claim 1,
   wherein, in the case where a composition formula of the unknown substance is given as additional information, narrowing of the candidates for the post-elimination structural formula by utilizing a composition of the eliminating partial structure determined from a difference between a composition of the unknown substance and the additional partial structure in the post-elimination structure estimating step.

4. The method for mass spectrometry data analysis according to claim 1,
   wherein, in the case where a composition formula or a structural formula of at least one of product ions originating from the unknown substance is given as additional information, estimation of structural formulas of some product ions can be omitted or narrowing of the candidates for structural formulas of some product ions by utilizing the additional information in the product ion structure estimating step.

5. The method for mass spectrometry data analysis according to claim 1,
   wherein, in the case where there are a plurality of candidates for the post-elimination structural formula estimated in the post-elimination structure estimating step, the structural formula of the unknown substance is estimated for each of the plurality of the candidates for the post-elimination structural formula in the product ion structure estimating step and the unknown substance structure estimating step, and a plurality of candidates for the structural formula are determined.

6. The method for mass spectrometry data analysis according to claim 1,
   wherein a plurality of candidates for the structural formula of the unknown substance are ranked in descending order of probability and the candidates for the structural formula are output together with the ranking.

7. The method for mass spectrometry data analysis according to claim 1,
   wherein the structural formula of the unknown substance is estimated after determining, as a candidate for the structural formula of one product ion from the unknown substance, the estimated structural formula obtained by performing each of the steps for an MS$^{n+1}$ spectrum obtained by MS$^{n+1}$ analysis performed using an ion having a specific mass-to-charge ratio in the MS$^n$ spectrum of the unknown substance as a precursor ion.

8. The method for mass spectrometry data analysis according to claim 1,
   wherein candidates for the structural formula of the unknown substance are determined using a plurality of MS$^n$ spectra obtained under different analysis conditions for the unknown substance, and a candidate obtained commonly among the different analysis conditions is output as an estimated result of the structural formula of the unknown substance.

9. A system for mass spectrometry data analysis for estimating a structure of an unknown substance produced through partial structural change from a known substance having a known structure based on MS$^n$ spectra (where n is an integer equal to or greater than 1) obtained by performing mass spectrometry of a product ions produced by dissociating, in one or a plurality of times, a precursor ion or ions originating from the unknown substance, the system comprising:

a) an additional partial structure information obtaining unit of obtaining pre-given information of an additional partial structure that can be added to the known substance in association with the structural change;

b) a post-elimination structure estimating unit of estimating a post-elimination structural formula after an unknown eliminating partial structure is eliminated from the known substance in association with the structural change, the estimation being performed based on pre-given information about structural formula of the known substance, information about an additional partial structure obtained by the additional partial structure information obtaining unit, and information about a mass of the precursor ion from the unknown substance obtained from a mass spectrum of the unknown substance;

c) a product ion structure estimating unit of estimating a structural formula of each of product ions by searching for coincidence of combined masses of a trunk partial structure and the additional partial structure and masses of product ions obtained from an $MS^n$ spectrum or $MS^n$ spectra of the unknown substance, the trunk partial structure being derived from a structure shown by a structural formula of candidates for the post-elimination structure formula estimated in the post-elimination structure estimating unit, and listing candidates for structural formulas of the product ions; and d) an unknown substance structure determining unit of determining a structural formula of the unknown substance by searching, based on the candidates for structural formulas of the product ions estimated by the product ion structure estimating unit, for a structural formula that can produce the candidates for the structural formulas of product ions by dissociation.

* * * * *